United States Patent [19]

Opie

[11] Patent Number: 4,570,003
[45] Date of Patent: Feb. 11, 1986

[54] PROCESS FOR THE PREPARATION OF 4-HYDROXY-6-METHYL-2-PYRONE

[75] Inventor: Thomas R. Opie, Collingswood, N.J.

[73] Assignee: Rohm and Haas Company, Philadelphia, Pa.

[21] Appl. No.: 384,854

[22] Filed: Jun. 4, 1982

Related U.S. Application Data

[63] Continuation-in-part of Ser. No. 236,352, Feb. 20, 1981, abandoned.

[51] Int. Cl.[4] .............................................. C07D 309/30
[52] U.S. Cl. ....................................................... 549/292
[58] Field of Search ........................................ 549/292

[56] References Cited

U.S. PATENT DOCUMENTS

| | | | |
|---|---|---|---|
| 2,034,303 | 3/1936 | Krzikalla et al. | 260/152 |
| 3,657,426 | 4/1972 | Schroeder | 424/200 |
| 3,926,970 | 2/1975 | Sauter | 542/441 |

FOREIGN PATENT DOCUMENTS

| | | |
|---|---|---|
| 2808795 | 9/1978 | Fed. Rep. of Germany . |
| 56409 | 4/1974 | Romania . |

OTHER PUBLICATIONS

Wiley and Jarboe, *J. Amer. Chem. Soc.*, 78, 624 (1955).
Suzuki, Sekizaki and Inoue, *Synthesis*, 652, (1975).
Abe, Nonomura, *Nippon Nogei Kagaku Kaishi*, 42, 591 (1968).
Borsche and Blount, Berichte der Deutschen Chemischen Gesellschaft, 65, 827, (1932).
Collie, *J. Chem. Soc.*, 59, 607–609 (1891).
Collie and Hilditch, *J. Chem. Soc.*, 91, 787 (1907).
Gostea et al., *Chemical Abstracts*, 82: 57575p (1975).
R. Bacardit et al., *Chemistry Letters*, (1), 5–6 (1982).
G. Le Guillanton, *Bull. Soc. Chim. Fr.*, (3–4, Pt. 2) 627–631, (1974) (Fr.).
Arndt and Aran, *Chem. Ber.*, 84, 343–347 at 346 (1951).
E. Marcus et al., *J. Heterocyclic Chem.*, 6, 13–22 at 20 (1969).
R. Bacardit et al., *J. Heterocyclic Chem.*, 19, 157 (1982).

*Primary Examiner*—Jane T. Fan
*Attorney, Agent, or Firm*—Terence P. Strobaugh

[57] ABSTRACT

This invention relates to a novel process for the preparation of 4-hydroxy-6-methyl-2-pyrone which comprises reacting 3-acetyl-6-methyl-2(H)-pyran-2,4(3H)-dione (dehydroacetic acid, "DHAA") with from 93% to about 99% sulfuric acid (1–7% water content) at temperatures from about 60° to about 140° C. under pressures from about 10 millimeters of mercury to about 75 pounds per square inch wherein the sulfuric acid to pyran weight ratio ($H_2SO_4$:DHAA) is from about 0.8:1 to about 3:1 and isolating the 4-hydroxy-6-methyl-2-pyrone.

6 Claims, No Drawings

PROCESS FOR THE PREPARATION OF 4-HYDROXY-6-METHYL-2-PYRONE

This is a continuation-in-part of U.S. Ser. No. 236,352, filed Feb. 20, 1981, now abandoned.

BACKGROUND OF THE INVENTION

The compound 4-hydroxy-6-methyl-2-pyrone (HMEP) has been used as an intermediate in the production of experimental azo dyes, nematocides, and mercocarbocyanine filter dyes. These uses are disclosed in U.S. Pat. No. 2,034,303, by H. Krzikalla and B. Eistert, assigned to General Aniline Works, Inc., Mar. 17, 1936; U.S. Pat. No. 3,657,426, by P. H. Schroeder, assigned to FMC Corporation, Apr. 18, 1972; and U.S. Pat. No. 3,926,970, by F. Sauter, assigned to Eastman Kodak Company, Dec. 15, 1975, respectively. HMEP has been used as an intermediate for the preparation of 1-(4-chlorophenyl)-1,4-dihydro-6-methyl-4-oxo-3-pyridazine carboxylates and related plant growth regulating agents. These uses are disclosed in German Offenlegungsschrift No. 2,808,795, by T. T. Fujimoto, assigned to Rohm and Haas Company, Sept. 14, 1978; and R. H. Wiley and C. H. Jarboe, *J. Amer. Chem. Soc.*, 78, 624 (1955), respectively.

HMEP has been prepared by (1) decarboxylation of its 3-carboxy derivatives; see E. Suzuki, H. Sekizaki, and Shoji Inoue, *Synthesis*, 652, 1975; (2) by enzymatic deacetylation of dehydroacetic acid, see K. Abe, S. Nonomura, and C. Tatsumi, *Nippon Nogei Kagaku Kaishi*, 42, 591 (1968); and (3) deacetylation of dehydroacetic acid (DHAA) in hot 90% sulfuric acid, see W. Borsche and B. K. Blount, *Berichte der Deutschen Chemischen Gesellschaft*, 65, 827 (1932), J. N. Collie, *J. Chem. Soc.*, 59, 607–609 (1891) and U.S. Pat. No. 3,657,426, supra.

Only the preparation in sulfuric acid appears to have commercial promise. The acidic deacetylation conditions by this procedure are critical since heating DHAA in 85% sulfuric acid produces primarily the rearrangement product 2,6-dimethyl-4-pyrone-3-carboxylic acid; see J. N. Collie and T. P. Hilditch, *J. Chem. Soc.*, 91, 787 (1907). Heating in concentrated hydrochloric acid produces 2,6-dimethyl-4-pyrone hydrochloride; see J. N. Collie, *J. Chem. Soc.*, 59, 619 (1981) and Romanian Pat. No. 56,409, by T. Gostea and A. Maza, assigned to Institutul de Cercetari Chimico-Farmaceutice, Apr. 15, 1974.

The preparation of HMEP from DHAA in sulfuric acid as disclosed by J. N. Collie is described in more detail by Borsche and Blount. The Collie-Borsche-Blount procedure is not suitable for batch production of HMEP because of the enormous rates of heat transfer that would be required. It or any other procedure requiring such large ratios of $H_2SO_4$ (3 to 1) and quench water (4 to 1) to DHAA suffers from problems of HMEP losses in the quench mixture, large volumes of acidic waste to be treated or recycled, and low kettle productivity. Moreover, the procedures are run under conditions (ca. two minutes at 130° C. or an unspecified time at 120° C.) that cannot readily be duplicated or controlled on a commercial scale.

SUMMARY OF THE INVENTION

This invention relates to a process for the preparation of 4-hydroxy-6-methyl-2-pyrone (HMEP) which comprises reacting dehydroacetic acid (DHAA) with an aqueous sulfuric acid solution containing from about 93% to about 95% sulfuric acid at reaction temperatures from about 60° to about 140° C. under pressures from about 10 mm Hg to about 6 kg/cm$^2$ (75 psig) wherein the $H_2SO_4$:DHAA weight ratio, based on actual $H_2SO_4$ weight content, is from about 0.8:1 to about 3:1. The time for which the reaction is carried out varies with the temperature and pressure used. Preferably, the $H_2SO_4$:DHAA weight ratio is from about 1.5:1 to about 2.5:1, the reaction temperature is from about 80° C. to about 120° C., and the reaction pressure is ambient pressure of about 1 kg/cm$^2$. More preferably, the reaction temperature is from about 95° C. to about 105° C. Preferably, the DHAA is reacted with an aqueous solution containing about 94% by weight of $H_2SO_4$. It is to be understood that the aqueous solution of $H_2SO_4$ may be prepared by diluting concentrated $H_2SO_4$ solution.

In another aspect, the process of this invention may be carried out by initially reacting the DHAA with an aqueous sulfuric acid solution containing from about 93 to about 99% sulfuric acid at reaction temperatures from about 60° C. to about 140° C. under pressures from about 10 mm Hg to about 6 kg/cm$^2$ wherein the $H_2SO_4$:DHAA weight ratio is from about 0.8:1 to about 3:1, based on actual $H_2SO_4$ weight content, followed by adding one or more incremental water conditions during the reaction whereby the total of incremental water added together with the water initially present is from about 4% to about 9% by weight of the total of water and sulfuric acid. Preferably, the total of incremental water added and water initially present is from about 4% to about 7% of the weight of total water and sulfuric acid, the reaction time is from about 3 minutes to about 15 hours, the reaction pressure is about 1 atmosphere (1 kg/cm$^2$), the $H_2SO_4$:DHAA ratio is from about 1.5:1 to about 2.5:1, and the reaction temperature is from about 80° C. to about 120° C.

The process of the present invention can be carried out either as a batch process or as a continuous process.

The more preferred aspect of the process of the present invention comprises initially reacting the DHAA with an aqueous sulfuric acid solution containing from about 94 to about 99% sulfuric acid and adding one or more incremental additions of water whereby the total of incremental water added together with the water initially present is from about 4% to about 7% by weight of the total of water and sulfuric acid, the reaction time being from about 10 minutes to about 15 hours and the reaction pressure being about one atmosphere.

The difference of the present invention over the prior art is that the present invention consists of controlling the water content of the sulfuric acid utilized in the HMEP preparation so that the initial sulfuric acid concentration is between 93% and 99%, and the total of water used in the reaction is from about 4% to about 9% by weight of the total of water and sulfuric acid.

The advantages of this invention over the prior art, which constitute a novel and commercially practical process for deacetylation of DHAA to afford HMEP, include the following:

1. Lower minimum $H_2SO_4$:DHAA charge ratios resulting in reduced waste volumes and higher productivity.

By use of that process involving incremental water additions to an initial charge of 1.4–2.2 parts by weight of 96.9–97.5% $H_2SO_4$ per part by weight of DHAA, the invention affords isolated HMEP yields of 71–80% after 2.1–2.5 hours at 100° C. (See Examples 1–5). The charge ratios represent 47%–73% of the sulfuric acid charge utilized in the Collie-Borsche-Blount procedure. This improvement further permitted 25%–38% reductions in the weight of quench water utilized. The overall result is a large reduction in the volume of acidic waste produced and a large increase in kettle productivities;

2. Increased yield and selectivity compared with that obtained using 90% sulfuric acid, especially at sulfuric acid:DHAA weight ratios of 2.5:1 or less.

The isolated HMEP yields of 71–80% mentioned above obtained in the process using incremental water additions and the isolated HMEP yield of 75% obtained using in the initial charge 94% $H_2SO_4$ wherein the $H_2SO_4$:DHAA weight ratio is 2.0:1 are higher than most of the yields reported using the Collie-Borsche-Blount procedure. In addition, they are much higher than the isolated HMEP yields obtaining using 90% sulfuric acid at 100° C. with lower sulfuric acid:DHAA weight ratios. For example, use of 90% sulfuric acid to provide a $H_2SO_4$:DHAA weight ratio of 1.58:1 gave a yield of HMEP, corrected for purity, of only 32% (Example 9). Thus, the use of the drier sulfuric acid according to the process of this invention, greatly improves the yield and selectivity of HMEP production.

3. Ready applicability to batch or continuous processing.

The lower reaction temperature and improved control of the water content of the sulfuric acid in this invention gives a process which is applicable to batch or continuous processing. Several 300-gallon scale batches of HMEP have been conducted using a preferred version of the invention (see Example 10).

The required concentration for the initial charge of the aqueous solution of sulfuric acid can be obtained by diluting concentrated sulfuric acid to the desired concentration. It is to be understood that the initial charge of the sulfuric acid can be obtained by diluting with water fuming sulfuric acid (also known as oleum) or a mixture of concentrated sulfuric acid and fuming sulfuric acid.

The present invention consists of controlling the water content of the sulfuric acid so that the initial sulfuric acid concentration is between 93% and 99%. Some advantage over the prior art in terms of amount and purity of product obtained are achieved by the use of relatively dry sulfuric acid solutions containing 93–95 weight percent of $H_2SO_4$. Especial advantages in amount and purity of product are achieved by the use of relatively dry sulfuric acid solutions wherein water is incrementally added whereby the total of incremental water together with the water initially present in the charge of the aqueous sulfuric acid solution is about 4% to about 9% by weight of the total of water and sulfuric acid.

It further consists of reductions in the reaction temperature and lengthening of heating and cooling cycles to permit a more readily controlled deacetylation. The invention is based upon the discovery that keeping the acid drier than the 90% sulfuric acid utilized in the prior art permits a more selective, practical preparation of HMEP to occur at lower sulfuric acid:DHAA ratios. That is, the advantages of the invention are achieved when the total of the water present in the initial charge and the incremental water added, if any, is about 4–9% by weight of the total of water and sulfuric acid. The preparation is especially selective if the reaction is initiated with relatively dry aqueous solution of sulfuric acid containing about 97% by weight of $H_2SO_4$ and small incremental portions of water are added thereafter during the course of the deacetylation reaction to bring the total water content up to the equivalent of starting with 93%–95% sulfuric acid.

If, however, the acid is too dry (e.g., 97% sulfuric acid with no incremental water additions), the deacetylation reaction stalls and much unconverted DHAA remains, especially when the $H_2SO_4$:DHAA weight ratio is less than about 2.5 to 1.0. On the other hand, when the acid utilized is too wet (e.g., the 90% sulfuric acid utilized in the prior art), the yield of the undesirable by-products 2,6-dimethyl-4-pyrone-3-carboxylic acid (DMPCA) and 2,6-dimethyl-4-pyrone (DMP) increases, especially if the $H_2SO_4$:DHAA weight ratio is less than about 2.5 to 1.0.

The following examples are illustrative of but a few aspects of the process of the present invention and are not to be considered in any way as being limitations on the breadth and scope thereof.

All experiments, except Examples 1, 2, and 10, were conducted in the laboratory using a stoppered 300 ml three-neck, round-bottom flask equipped with a mechanical paddle stirrer and a thermometer. The flask was heated by a heating mantle controlled by an Instruments for Research and Industry Therm-o-Watch ® controller. Example 2 was carried out in a 1 liter, 4-necked, round-bottom flask fitted with a mechanical stirring apparatus, addition funnel, and thermometer. Examples 1 and 10 were run in 10-gallon and 300-gallon glass-lined kettles, respectively, and the kettles were heated with steam or tempered water. In all cases, except Examples 1 and 10, the dehydroacetic acid was charged before the sulfuric acid, but the order of addition is immaterial to the invention.

Quenches of the reaction mixtures were conducted using 1.39 or 1.77 parts by weight of quench water per part by weight of sulfuric acid (100% basis) used. The decrease in yields of HMEP product corrected for purity using the lower quench ratio was only 0.6%. The amounts of DHAA, HMEP, DMPCA, and DMP in the unquenched reaction mixtures were determined by NMR spectroscopy of the pyrone ring vinyl proton absorption signals, or peaks, at $\delta$ 5.5–7.5.

EXAMPLE 1

14.7 lbs. of dehydroacetic acid and 29.2 lbs. of 96.9% sulfuric acid were charged to an unpressurized glass-lined 10-gallon kettle and heated with stirring over 65 minutes to 98° C. Then the mixture was held for 2.5 hours at 96°–98° C. Two five-ounce tap water charges were added after 30 and 60 minutes of the hold period had elapsed; during the hold period, the color of the reaction mixture changed from a golden brown to a reddish brown. One-ounce samples were taken for NMR analysis after one hour and two hours of the hold period had elapsed.

After the 2.5 hour hold, the agitated reaction mixture was cooled to 22° C. over 65 minutes. Then 50.2 lbs. of tap water were added to the reaction mixture over 105 minutes at 22°–46° C.; a finely divided white slurry of HMEP precipitated. The HMEP slurry was cooled to 10° C. and filtered onto a chock filter equipped with a cheesecloth. The wet cake was washed with two 22.0 lb. portions of tap water and sucked dry to give 16.7 lbs. of 49.7% solids wet HMEP. The crude isolated yield of HMEP was 8.3 lbs. (75.6%); the purity of a sample of the HMEP was 98–101%, that is, about 98% (four determinations) by TLC densitometry. NMR analysis of the two-hour sample indicated a 78.5% reaction yield of HMEP and a 14.5% yield of DMPCA with 7.0% unconverted DHAA. The yield of HMEP corrected for purity was then 74% (0.98×0.756=0.74).

EXAMPLE 2

Example 2 was the first reduction to practice of the invention. 111.3 g of DHAA and 220.4 g of 96.9% $H_2SO_4$ were charged to a 1,000 ml, 4-necked, round-bottom flask equipped with an additional funnel, paddle stirrer, and thermometer. The stirrer mixture was rapidly heated to 110° C. and held for 5 hours at 109°–112° C. After 3 hours, a 1.807 g water charge was added, after 4.27 hours, a second 1.807 g water charge was added. Four NMR samples removed during the hold period gave the following analysis:

| Time | % DHAA | % HMEP | % DMPCA |
| --- | --- | --- | --- |
| 45 min. | 34.5 | 54.5 | 11.0 |
| 2.5 hr. | 26.9 | 57.2 | 15.9 |
| 3.75 hr. | 7.5 | 74.8 | 17.7 |
| 5.0 hr. | 2.7 | 79.5 | 18.8 |

At the end of the hold period, the mixture was cooled and quenched with 380 g of tap water at 20.0°–52.5° C. over 28 minutes. The resulting white HMEP slurry was cooled to, and then held for one hour, at 0°–5° C. and then it was suction filtered to give a HMEP wet cake.

The HMEP was washed twice with 165 g portions of tap water and vacuum dried to give 62.4 g (75.6% yield). The purity of product was determined by TLC densitometry to be 95.4% pure dry HMEP. The corrected HMEP yield was 72%.

Table I summarizes the conditions used in Examples 1 and 2, as well as Examples 3–7 and 10 illustrative of the invention; Examples 8 and 9, illustrative of prior art processes, are set forth for comparison purposes.

Examples 3–6 and 10 in Table I further illustrate the advantages of the use of one or more incremental water additions and low $H_2SO_4$:DHAA ratios according to the more preferred aspect of this invention.

Example 7 illustrates the reparation of HMEP according to this invention using a $H_2SO_4$:DHAA weight ratio of 2.0:1.0 wherein the initial charge of aqueous sulfuric acid was a 94% $H_2SO_4$ aqueous solution.

Examples 8 and 9 in Table I illustrate the preparation of HMEP at lower temperatures and lower sulfuric acid ratios using the 90% sulfuric acid set forth in the prior art. The yields of HMEP obtained are clearly lower than those obtained using similar $H_2SO_4$:DHAA ratios under the drier conditions of this invention.

Example 10 illustrates the large scale preparation of HMEP using one of the preferred sets of conditions of this invention.

The results of these experiments are presented in Table II below.

TABLE I

Preparations of HMEP by Deacetylation of DHAA
Summary of Reaction Conditions

| Example | Reaction Time | Reaction Temp., °C. | Amount (wt.) Initial Aq. $H_2SO_4$ Soln. | Init. Conc. of Aq. Soln. of $H_2SO_4$ | Amount (wt.) (Initial) of DHAA | Water Charges Amount, Time of Charge |
| --- | --- | --- | --- | --- | --- | --- |
| 1 | 2.5 hr. | 96–98 | 29.2 lb. | 96.9% | 14.7 lb. | 0.31 lb., 30 min. |
|   |         |       |          |        |          | 0.31 lb., 60 min. |
| 2 | 5.0 hr. | 109–112 | 220.4 g. | 96.9 | 111.3 g. | 1.81 g., 3 hr. |
|   |         |       |          |        |          | 1.80 g., 4.27 hr. |
| 3 | 1.0 hr. | 98–105 | 110.5 g. | 97.1 | 50.4 g. | 1.01 g., 30 min. |
| 4 | 2.0 hr. | 98–105 | 81.5 g.[a] | 97.5 | 50.43 g. | 0.94 g., 30 min. |
|   |         |       |          |        |          | 0.95 g., 60 min. |
| 5 | 2.5 hr. | 96–103 | 71.1 g | 96.9 | 50.4 g. | 0.96 g., 21 min. |
|   |         |       |          |        |          | 0.77 g., 60 min. |
|   |         |       |          |        |          | 0.81 g., 105 min. |
| 6 | 3.1 hr. | 98–103 | 52.9 g.[b] | 99.1 | 50.45 g. | 0.72 g., 30 min. |
|   |         |       |          |        |          | 0.68 g., 62 min. |
|   |         |       |          |        |          | 0.29 g., 122 min. |
| 7 | 2.1 hr. | 99–106 | 103.0 g.[c] | 94.0 | 50.4 g. | none |
| 8 | 2.0 hr. | 99–105 | 119.2 g.[d] | 90.0 | 50.4 g. | none |
| 9 | 2.0 hr. | 99–105 | 97.9 g.[e] | 90.0 | 55.95 g. | none |
| 10 | 3.65 hr. | 98–111 | 983.3 lb.[f] | 97.1 | 496.0 lb. | 13.5 lb., 30 min. |
|   |         |       |          |        |          | 13.5 lb., 60 min. |

[a]Actual charge was 76.7 g. of 97.1% $H_2SO_4$ plus 4.80 g. of 104.1% $H_2SO_4$ (20% oleum or fuming $H_2SO_4$)
[b]Actual charge was 37.85 g. of 97.1% $H_2SO_4$ 15.05 g. of 104.1% $H_2SO_4$ (20% oleum or fuming $H_2SO_4$)
[c]Actual charge was 100.8 g. of 96.0% $H_2SO_4$ plus 2.2 g. of $H_2O$
[d]Actual charge was 111.8 g. of 96.0% $H_2SO_4$ plus 7.4 g. of $H_2O$
[e]Actual charge was 98.8 g. of 96.0% $H_2SO_4$ plus 6.1 g. of $H_2O$
[f]Actual charge was 500 lb. of 99.1% $H_2SO_4$ plus 475 lb. of 96.6% $H_2SO_4$ plus 7.8 lb of $H_2O$

TABLE II

Distribution of Reaction Mixture Components

| EXAMPLE NO. | Mole %[a] of Reaction Mixture Components at End of Hold Period | | | | Analysis of Isolated Products | | |
| --- | --- | --- | --- | --- | --- | --- | --- |
|   | HMEP | DHAA | DMPCA[b] | DMP[c] | Crude Yield | Product Purity % HMEP[d] | Yield of HMEP Corrected for Purity (%) |
| 1 | 78.5 | 7.0 | 14.5 | — | 8.3 lb., 75.6% | 98 | 74 |
| 2 | 79.5 | 2.7 | 18.8 | — | 62.4 g., 75.5% | 95 | 72 |
| 3 | 91.1 | 0.0 | 8.9 | — | 30.4 g., 80.4% | — | — |
| 4 | 81.0 | 4.3 | 14.7 | — | 28.4 g., 75.0% | 101 | 75 |
| 5 | 83.9 | 0.0 | 16.1 | — | 27.8 g., 73.7% | 97 | 71 |
| 6 |      |     |      |   | 20.5 g., 54.2% | 101 | 54 |
| 7 | 74.9 | 9.1 | 12.8 | 3.3 | 28.4 g., 75.1% | 101 | 75 |
| 8 | 69.3 | 0.6 | 25.8 | 4.4 | 23.0 g., 61.0% | 99 | 61 |

TABLE II-continued

| | Distribution of Reaction Mixture Components | | | | | | |
|---|---|---|---|---|---|---|---|
| | Mole %[a] of Reaction Mixture Components at End of Hold Period | | | | | Analysis of Isolated Products | |
| | | | | | | Product Purity | Yield of HMEP Corrected for |
| EXAMPLE NO. | HMEP | DHAA | DMPCA[b] | DMP[c] | Crude Yield | % HMEP[d] | Purity (%) |
| 9 | 43.9 | 0.0 | 43.5 | 12.6 | 14.3 g., 34.1% | 94 | 32 |
| 10 | 88.6 | 4.1 | 9.35 | — | 296 lb., 79.5% | 101 | 80 |

[a]Mole % of reaction mixture components determined by nmr analysis.
[b]DMPCA is 2,6-dimethyl-4-pyrone-3-carboxylic acid.
[c]DMP is 2,6-dimethyl-4-pyrone.
[d]Product Purity - % HMEP determined by quantitative thin layer chromatography (tlc) (%). Standard deviation of the analytical method is ± 1%.
[e]Yield of HMEP corrected for purity = Crude Yield × Product Purity (%).

The results set forth in Table II show that the process illustrated in Example 7 according to the invention, wherein an aqueous sulfuric acid solution containing 94% by weight of $H_2SO_4$:DHAA ratio was about 2:1 and wherein no incremental water additions were used, afforded a much higher yield of desired HMEP and much lower levels of by-products than was obtained by comparison Examples 8 and 9.

The results set forth in Table II show that the process illustrated in Examples 1–5 and 10 according to the invention, wherein the DHAA is initially reacted with an aqueous sulfuric acid solution containing 93–99% by weight of $H_2SO_4$ followed by the addition of one or more incremental water additions wherein the $H_2SO_4$:DHAA ratio was from 1.37:1 to 2.13:1 and wherein the total water was 4–7% of the total of the water and sulfuric acid, generally afforded a much higher yield of desired HMEP and much lower levels of by-products than was obtained by comparison Examples 8 and 9.

In Examples 6 according to the process of the invention illustrated in Examples 1–5 and 10 using incremental water additions except that the $H_2SO_4$:DHAA ratio was about 1:1, a 54% yield of HMEP was obtained in comparison Examples 8 and 9. Analysis to determine the composition of the reaction mixture was not performed. Accordingly, the significance of the results of Examples 6 is not fully understood when considered in light of the results in Examples 1–5 and 10.

Table III summarizes the weight ratio of $H_2SO_4$:DHAA, the initial concentration (%) of $H_2SO_4$ in the starting aqueous sulfuric acid solution, and the total of the water (initial and water added, if any) in the reaction mixture.

TABLE III

| | $H_2SO_4$:DHAA Ratio and Amounts of $H_2SO_4$ and Water | | |
|---|---|---|---|
| Example No. | $H_2SO_4$:DHAA Ratio | Initial Conc. (%) of $H_2SO_4$ Solu. | Total Water (%) |
| 1 | 1.92:1 | 96.9 | 5.1 |
| 2 | 1.92:1 | 96.9 | 4.7 |
| 3 | 2.13:1 | 97.1 | 3.8 |
| 4 | 1.58:1 | 97.5 | 4.7 |
| 5 | 1.37:1 | 96.9 | 6.4 |
| 6 | 1.04:1 | 99.1 | 4.0 |
| 7 | 1.92:1 | 94 | 6.0 (n. a.)* |
| 8 | 2.13:1 | 90 | 10.0 (n. a.) |
| 9 | 1.58:1 | 90 | 10.0 (n. a.) |
| 10 | 1.92:1 | 97.1 | 5.5 |

*n.a. = no addition

The obvious modifications of the process of the present invention which are within the realm of one skilled in the art are meant to be encompassed by the invention as disclosed herein and as claimed in the claim appended hereto.

What is claimed is:

1. A process for the preparation of 4-hydroxy-6-methyl-2-pyrone which comprises reacting dehydroacetic acid (DHAA) with an aqueous sulfuric acid solution containing from about 93% to about 95% by weight of sulfuric acid ($H_2SO_4$) at reaction temperatures of from about 60° C. to about 140° C. under pressures from about 10 mm Hg to about 6 kg/cm² wherein the $H_2SO_4$:DHAA weight ratio, based on actual $H_2SO_4$ weight content, is from about 0.8:1 to about 3:1.

2. A process according to claim 1 wherein the $H_2SO_4$:DHAA ratio is from about 1.5:1 to about 2.5:1, the reaction temperature is from about 80° C. to about 120° C., and the reaction pressure is ambient atmospheric pressure of about 1 kg/cm².

3. A process according to claim 2 wherein the reaction temperature is from about 95° C. to about 105° C.

4. A process according to claim 2 wherein the DHAA is initially reacted with an aqueous solution containing about 94% by weight of $H_2SO_4$.

5. A process for the preparation of 4-hydroxy-6-methyl-2-pyrone which comprises initially reacting dehydroacetic acid (DHAA) with an aqueous sulfuric acid solution containing from about 93% to about 99% by weight of sulfuric acid ($H_2SO_4$) at reaction temperatures from about 60° to about 140° under pressures from about 10 mm Hg to about 6 kg/cm² wherein the $H_2SO_4$:DHAA weight ratio is from about 0.8:1 to about 3:1, based on actual $H_2SO_4$ weight content, followed by adding one or more incremental water additions during the reaction whereby the total of incremental water added together with the water initially present is from about 4% to about 9% by weight of the total of water and sulfuric acid.

6. A process according to claim 5 wherein the total water is from about 4% to about 7% of the weight of total water and sulfuric acid, the reaction time is from about 3 minutes to about 16 hours, the reaction pressure is about one atmosphere (1 kg/cm²), the $H_2SO_4$:DHAA weight ratio is from about 1.5:1 to about 2.5:1, and the reaction temperature is from about 80° C. to about 120° C.

* * * * *